United States Patent
Funke et al.

(10) Patent No.: US 6,417,353 B1
(45) Date of Patent: Jul. 9, 2002

(54) PREPARING AMINES

(75) Inventors: Frank Funke, Limburgerhof; Joachim Wulff-Döring, Frankenthal; Gerhard Schulz, Ludwigshafen; Wolfgang Siegel, Limburgerhof; Andreas Kramer, Freinsheim; Johann-Peter Melder, Böhl-Iggelheim; Arthur Höhn, Kircheim, all of (DE); Philipp Buskens, Hoogstraaten (BE); Wolfgang Reif, Frankenthal; Jan Nouwen, Wachenheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/520,908

(22) Filed: Mar. 7, 2000

(30) Foreign Application Priority Data

May 3, 1999 (DE) .......................... 199 10 960

(51) Int. Cl.$^7$ .............................. C07B 43/04
(52) U.S. Cl. ................. 540/450; 540/467; 540/470; 540/533; 540/544; 540/575; 540/596; 540/610; 540/612; 544/88; 544/106; 544/242; 544/392; 544/410; 546/184; 546/192; 546/207; 548/215; 548/300.1; 548/577; 548/578; 548/579; 548/950; 564/373; 564/374; 564/384; 564/397
(58) Field of Search .................. 564/397, 373, 564/374, 384; 540/450, 467, 470, 533, 544, 575, 596, 610, 612; 544/88, 106, 242, 392, 410; 546/184, 192; 548/207, 215, 360.1, 572, 578, 579, 950, 951

(56) References Cited

U.S. PATENT DOCUMENTS

| | | | |
|---|---|---|---|
| 4,152,353 A | 5/1979 | Habenmann | 260/585 |
| 4,206,150 A * | 6/1980 | Slaugh | 260/583 R |
| 4,234,727 A | 11/1980 | Toussaint et al. | 544/178 |
| 4,536,577 A * | 8/1985 | Yoshida et al. | 544/326 |
| 5,002,922 A | 3/1991 | Irgang et al. | 502/331 |
| 5,530,127 A * | 6/1996 | Reif et al. | 544/106 |
| 5,608,113 A | 3/1997 | Becker et al. | 564/480 |
| 5,910,612 A * | 6/1999 | Simon et al. | 564/497 |

FOREIGN PATENT DOCUMENTS

| | | |
|---|---|---|
| DE | 28 38 184 | 3/1960 |
| DE | 26 18 580 | 11/1977 |
| EP | 017 651 | 10/1980 |
| EP | 382 049 | 8/1990 |
| EP | 487 514 | 5/1992 |
| EP | 514 692 | 11/1992 |
| EP | 696 572 | 2/1996 |
| EP | 697 395 | 2/1996 |
| EP | 861 824 | 9/1998 |
| EP | 861824 A1 * | 9/1998 |
| EP | 905 122 | 3/1999 |
| EP | 963 975 | 12/1999 |
| JP | 59042345 | 3/1994 |

OTHER PUBLICATIONS

Ullmann "Encyclopedia of Industrial Chemistry, vol. 5A", Gerhartz, W Exec. Ed., VCH Verlagsgellschaft, Weinheim, Germany, p. 352, 1986.*

* cited by examiner

Primary Examiner—Mukund J. Shah
Assistant Examiner—Thomas C McKenzie
(74) Attorney, Agent, or Firm—Keil & Weinkauf

(57) ABSTRACT

Amines are prepared by reacting aldehydes or ketones at elevated temperature under elevated pressure with nitrogen compounds selected from the group of ammonia, primary and secondary amines, and with hydrogen in the presence of a catalyst containing

- copper, wherein the catalytically active mass of the catalyst contains, before the reduction with hydrogen,
- 20 to 85% by weight of oxygen-containing compounds of zirconium, calculated as $ZrO_2$,
- 1 to 30% by weight of oxygen-containing compounds of copper, calculated as CuO,
- 14 to 70% by weight of oxygen-containing compounds of nickel, calculated as NiO,
- 0 to 5% by weight of oxygen-containing compounds of molybdenum, calculated as $MoO_3$,
- and 0 to 10% by weight of oxygen-containing compounds of aluminum, calculated as $Al_2O_3$.

10 Claims, No Drawings

PREPARING AMINES

The present invention relates to a process for preparing amines by reacting aldehydes or ketones at elevated temperature under elevated pressure with nitrogen compounds selected from the group of ammonia, primary and secondary amines, and with hydrogen in the presence of a catalyst containing copper.

EP-A-514 692 discloses catalysts containing oxides of copper, nickel and/or cobalt, zirconium and/or aluminum for the catalytic amination of alcohols in the gas phase with ammonia or primary amines and hydrogen. This patent application discloses that the atomic ratio of nickel to copper in these catalysts must be from 0.1 to 1.0, preferably 0.2 to 0.5 (cf. loc. cit.: Example 1) since, otherwise, yield-reducing byproducts are formed to an increased extent in the amination of alcohols (loc. cit.: Examples 6 and 12). Aluminum oxide is preferably used as support (loc. cit.: Examples 1 to 5 and 7 to 11).

EP-A-382 049 discloses catalysts containing oxygen-containing zirconium, copper, cobalt and nickel compounds, and processes for the hydrogenating amination of alcohols. The preferred zirconium oxide content of these catalysts is 70 to 80% by weight (loc. cit.: page 2, last paragraph; page 3, $3^{rd}$ paragraph; Examples). Although these catalysts have good activity and selectivity, their useful lives are in need of improvement.

EP-A-696 572 and EP-A-697 395 disclose catalysts containing oxides of nickel, copper, zirconium and molybdenum for the catalytic amination of alcohols with nitrogen compounds in the presence of hydrogen.

The earlier German applications Nos. 19742911.4 of Sep. 29, 1997 and 19826396.1 of Jun. 12, 1998, relate to processes for preparing amines by reacting primary or secondary alcohols with nitrogen compounds selected from the group of ammonia, primary and secondary amines, at temperatures of from 80 to 250° C. under pressures of from 0.1 to 40 MPa with hydrogen in the presence of catalysts containing zirconium, copper and nickel.

DE-A-28 38 184 describes a process for preparing tertiary amines by reacting secondary amines with alcohols or carbonyl compounds under hydrogenating conditions in the gas phase, by undertaking the reaction of a copper catalyst which has been obtained by thermal decomposition and reduction of a basic copper aluminum carbonate.

It is an object of the present invention to improve, by remedying the disadvantages of the prior art, the economics of the processes used to date for the hydrogenating amination of aldehydes and ketones. It was intended to find catalysts which can be prepared industrially in a simple manner and which permit the hydrogenating amination of aldehydes and ketones to be carried out with high conversion and good yield, selectivity and catalyst life. The catalysts ought accordingly to have a high activity and a high mechanical stability under the reaction conditions.

We have found that this object is achieved by a process for preparing amines by reacting aldehydes or ketones at elevated temperature under elevated pressure with nitrogen compounds selected from the group of ammonia, primary and secondary amines, and with hydrogen in the presence of a catalyst containing copper, wherein the catalytically active mass of the catalyst contains, before the reduction with hydrogen, 20 to 85% by weight of oxygen-containing compounds of zirconium, calculated as $ZrO_2$, 1 to 30% by weight of oxygen-containing compounds of copper, calculated as CuO, 14 to 70% by weight of oxygen-containing compounds of nickel, calculated as NiO, 0 to 5% by weight of oxygen-containing compounds of molybdenum, calculated as $MoO_3$, and 0 to 10% by weight of oxygen-containing compounds of aluminum, calculated as $Al_2O_3$.

The catalysts in the process according to the invention are generally employed preferably in the form of catalysts which consist only of catalytically active mass and, where appropriate, a molding auxiliary (such as graphite or stearic acid) if the catalyst is employed as shaped articles, that is to say contain no other catalytically active constituents.

In this connection, the oxygen-containing compounds of zirconium and of aluminum which are used as support materials are regarded as belonging to the catalytically active mass.

The catalysts are employed in such a way that the catalytically active mass which has been ground to a powder is introduced into the reaction vessel, or that the catalytically active mass is arranged in the reactor after grinding, mixing with shaping auxiliaries, shaping and heat-treating as catalyst shaped articles—for example as tablets, beads, rings, extrudates (e.g. ribbons).

The concentrations (in % by weight) stated for the components of the catalyst are in each case—unless stated otherwise—based on the catalytically active mass of the finished catalyst after its last heat treatment and before its reduction with hydrogen.

The catalytically active mass of the catalyst after its last heat treatment and before its reduction with hydrogen is defined as the total of the masses of the catalytically active constituents and of the abovementioned catalyst support materials and essentially comprises the constituents of oxygen-containing compounds of zirconium, oxygen-containing compounds of copper, oxygen-containing compounds of nickel and, optionally, oxygen-containing compounds of molybdenum and/or oxygen-containing compounds of aluminum.

The total of the abovementioned constituents in the catalytically active mass, calculated as $ZrO_2$, CuO, NiO, $MoO_3$ and $Al_2O_3$, is normally from 70 to 100% by weight, preferably 80 to 100% by weight, particularly preferably 90 to 100% by weight, in particular 95 to 100% by weight, very particularly preferably 100% by weight.

The catalytically active mass of the catalysts employed in the process according to the invention may furthermore comprise one or more elements (oxidation state 0) or their inorganic or organic compounds selected from groups I A to VI A and I B to VII B and VIII of the periodic table. Examples of such elements or compounds thereof are: transition metals such as Co or CoO, Mn or manganese oxides, Re or rhenium oxides, Cr or chromium oxides, W or tungsten oxides, Ta or tantalum oxides, Nb or niobium oxides or niobium oxalate, V or vanadium oxides or vanadyl pyrophosphate; lanthanides such as Ce or $CeO_2$, or Pr or $Pr_2O_3$; alkali metal oxides such as $Na_2O$; alkali metal carbonates; alkaline earth metal oxides such as SrO; alkaline earth metal carbonates such as $MgCO_3$, $CaCO_3$ and $BaCO_3$; boron oxide ($B_2O_3$).

The catalytically active mass of the catalysts employed in the process according to the invention contains after the last heat treatment thereof and before the reduction with hydrogen 20 to 85% by weight, preferably 20 to 84.9% by weight, particularly preferably 22 to 65% by weight, very particularly preferably 25 to 49.7% by weight, of oxygen-containing compounds of zirconium, calculated as $ZrO_2$, 1 to 30% by weight, particularly preferably 5 to 25% by weight, very particularly preferably 10 to 25% by weight, of oxygen-containing compounds of copper, calculated as CuO, 14 to 70% by weight, particularly preferably 29.7 to 70% by weight, very particularly preferably 40 to 60% by weight, of oxygen-containing compounds of nickel, calculated as NiO, 0 to 5% by weight, preferably 0.1 to 5% by weight, particularly preferably 0.3 to 3.5% by weight, of oxygen-containing compounds of molybdenum, calculated as $MoO_3$, and 0 to 10% by weight, very particularly preferably 0 to 5% by weight, of oxygen-containing compounds of aluminum, calculated as $Al_2O_3$.

The content of oxygen-containing compounds of aluminum, calculated as $Al_2O_3$, in the catalytically active mass can be up to 10% by weight, and the ratio by weight of oxygen-containing compounds of zirconium, calculated as $ZrO_2$, to the oxygen-containing compounds of aluminum, calculated as $Al_2O_3$, is at least 2.2, preferably at least 2.5, particularly preferably at least 5.

The catalysts preferably employed in the process according to the invention have a catalytically active mass after the last heat treatment and before the reduction with hydrogen containing less than 20% by weight, preferably less than 10% by weight, in particular less than 5% by weight, very especially less than 1% by weight, of cobalt, calculated as CoO. The catalytically active mass very particularly preferably contains no catalytically active amounts of cobalt or its compounds.

In addition, the molar ratio of nickel, calculated as NiO, to copper, calculated as CuO, in the catalyst preferably employed in the process according to the invention is greater than 1, preferably greater than 1.2, particularly preferably 1.8 to 8.5.

Various procedures are possible for preparing the catalysts. They can be obtained, for example, by peptization of powdered mixtures of the hydroxides, carbonates, oxides and/or other salts of the components with water and subsequent extrusion and heat treatment of the mass obtained in this way.

However, precipitation methods are generally used to prepare the catalysts according to the invention. Thus, they can be obtained for example by a joint precipitation of the nickel and copper components from an aqueous salt solution containing these elements by use of mineral bases in the presence of a suspension of an oxygen-containing zirconium compound of low solubility, and subsequent washing, drying and calcining of the resulting precipitate. Examples of oxygen-containing zirconium compounds of low solubility which can be used are zirconium dioxide, zirconium oxide hydrate, zirconium phosphates, borates and silicates. The suspensions of the zirconium compounds of low solubility can be prepared by suspending fine-particle powders of these compounds in water with vigorous stirring. These suspensions are advantageously obtained by precipitating the zirconium compounds of low solubility from aqueous zirconium salt solutions with use of mineral bases.

The catalysts according to the invention are preferably prepared by a joint precipitation (coprecipitation) of all their components. This is expediently done by adding an aqueous mineral base, in particular an alkali metal base, for example sodium carbonate, sodium hydroxide, potassium carbonate or potassium hydroxide, to an aqueous salt solution containing the catalyst components at elevated temperature and with stirring until the precipitation is complete. The molybdenum is, where appropriate, preferably introduced subsequently. The nature of the salts used is generally not critical: since what mainly matters with this procedure is the solubility of the salts in water, one criterion is that they have a good solubility in water necessary to prepare these relatively highly concentrated salt solutions. It is regarded as self-evident that, when selecting the salts of the individual components, the salts chosen are, of course, only those with anions which do not interfere, whether by causing unwanted precipitations or by impeding or preventing the precipitation by complex formation.

The precipitates obtained in these precipitation reactions are generally not chemically homogeneous and consist, inter alia, of mixtures of the oxides, oxide hydrates, hydroxides, carbonates and insoluble and basic salts of the metals employed. It may prove to be beneficial for the filterability of the precipitates if they are aged, i.e. if they are left alone for some time after the precipitation, where appropriate at elevated temperature or while passing air through.

The precipitates obtained after these precipitation processes are further processed to the catalysts according to the invention in a conventional way. After washing, they are dried, generally at 80 to 200° C., preferably at 100 to 150° C., and then calcined. The calcination is generally carried out at temperatures between 300 and 800° C., preferably at 400 to 600° C., in particular at 450 to 550° C.

After the calcination, the catalyst is expediently conditioned, whether by grinding it to a particular particle size or admixed, after its grinding, with molding aids such as graphite or stearic acid, compressing to shaped articles by means of a tablet press, and heat treating. The temperatures of the heat treatment generally correspond to the temperatures for the calcination.

The catalysts prepared in this way contain the catalytically active metals in the form of a mixture of their oxygen-containing compounds, i.e. in particular as oxides and mixed oxides.

The catalysts prepared in this way are stored and, where appropriate, traded as such. Before being used as catalysts for the hydrogenating amination of aldehydes or ketones, they are normally reduced. However, they can also be employed without prior reduction, in which case they are reduced by the hydrogen present in the reactor under the conditions of the hydrogenating amination. For the prior reduction, the catalysts are generally first exposed to a nitrogen/hydrogen atmosphere at 150 to 200° C. over a period of 12 to 20 hours, and then treated in a hydrogen atmosphere at 200 to 400° C. for up to about 24 hours. In this prior reduction, some of the oxygen-containing metal compounds present in the catalysts are reduced to the corresponding metals, so that these are present, together with the various types of oxygen compounds, in the active form of the catalyst.

A particular advantage of the catalysts employed in the process according to the invention is their mechanical stability, i.e. their hardness. The mechanical stability is determined by the side crushing strength. To do this, the catalyst shaped article, e.g. the catalyst tablet, is exposed to an increasing force between two parallel plates, e.g. on the convex surface of the catalyst tablets, until the catalyst shaped article fractures. The force recorded when the catalyst shaped article fractures is the side crushing strength.

Amines of the general formula I

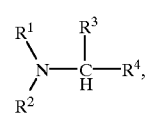

(I)

in which
R$^1$, R$^2$ are hydrogen, $C_{1-20}$-alkyl, $C_{3-12}$-cycloalkyl, aryl, $C_{7-20}$-aralkyl and $C_{7-20}$-alkylaryl or together are $(CH_2)_j$—X—$(CH_2)_k$,
R$^3$, R$^4$ are hydrogen, alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, alkanolaminoalkyl such as $C_{1-20}$-alkanolaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R^5$—$(OCR^6R^7CR^8R^9)_n$—$(OCR^6R^7)$, aryl, hetaryl, aralkyl such as $C_{7-20}$-aralkyl, hetarylalkyl such as $C_{4-20}$-hetarylalkyl, alkylaryl such as $C_{7-20}$-alkylaryl, alkylhetaryl such as $C_{4-20}$-alkylhetaryl and Y—$(CH_2)_m$—$NR^5$—$(CH_2)_q$ or together are $(CH_2)_l$—X—$(CH_2)_m$ or $R^2$ and $R^4$ are together $(CH_2)_l$—X—$(CH_2)_m$, $R^5$, $R^{10}$ are hydrogen, $C_{1-4}$-alkyl, $C_{7-40}$-alkylphenyl, $R^6$, $R^7$, $R^8$, $R^9$ are hydrogen, methyl or ethyl, X is $CH_2$, $CHR^5$, oxygen (O) or $NR^5$, Y is $N(R^{10})_2$, hydroxyl, $C_{2-20}$-alkylaminoalkyl or $C_{3-20}$-dialkylaminoalkyl, n is an integer from 1 to 30 and j, k, l, m, q are an integer from 1 to 4 are of particular commercial interest.

The process according to the invention is therefore preferably used to prepare amines I by reacting aldehydes or ketones of the formula II or III

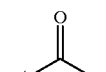

(II)

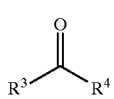

(III)

with nitrogen compounds of the general formula IV

(IV)

where $R^1$, $R^2$, $R^3$ and $R^4$ have the abovementioned meanings.

As is evident from the definitions for the radicals $R^2$ and $R^4$, an intramolecular reaction in an appropriate amino ketone or amino aldehyde is also possible.

The substituents $R^1$, $R^2$, $R^3$, $R^4$, $R^5$, $R^6$, $R^7$, $R^8$, $R^9$, $R^{10}$, the variables X, Y and the indices j, k, l, m, n and q in the compounds I, II, III and IV have, independently of one another, the following meanings:

$R^1$, $R^2$, $R^3$, $R^4$, $R^5$, $R^6$, $R^7$, $R^8$, $R^9$, $R^{10}$
hydrogen (H), $R^3$, $R^4$
$C_{1-200}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably isopropyl, 2-ethylhexyl, n-decyl, 2-n-propyl-n-heptyl, n-tridecyl, 2-n-butyl-n-nonyl and 3-n-butyl-n-nonyl, and preferably $C_{40-200}$-alkyl such as polybutyl, polyisobutyl, polypropyl, polyisopropyl and polyethyl, particularly preferably polybutyl and polyisobutyl, $C_{1-20}$-hydroxyalkyl, preferably $C_{1-8}$-hydroxyalkyl, particularly preferably $C_{1-4}$-hydroxyalkyl, such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl, $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(aminoethyl)aminoethyl and N-(aminoethyl)aminomethyl, $C_{1-20}$-hydroxyalkyl aminoalkyl, preferably $C_{1-8}$-hydroxyalkylaminoalkyl such as (2-hydroxyethylamino)methyl, 2-(2-hydroxyethylamino)ethyl and 3-(2-hydroxyethylamino) propyl, $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$- to $C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $R^5$—$(OCR^6R^7CR^8R^9)_n$—$(OCR^6R^7)$, preferably $R^5$—$(OCHR^7CHR^9)_n$—$(OCR^6R^7)$, particularly preferably $R^5$—$(OCH_2CHR^9)_n$—$(OCR^6R^7)$, $C_{3-30}$-dialkylaminoalkyl, preferably $C_{3-20}$-dialkylaminoalkyl, particularly preferably $C_{3-10}$-N,N-dialkylaminoalkyl such as N,N-dimethylaminomxethyl, 2-(N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, $(R^5)_2N$—$(CH_2)_q$, $C_{2-30}$-alkylaminoalkyl, preferably $C_{2-20}$-alkylaminoalkyl, particularly preferably $C_{2-8}$-alkylaminoalkyl such as methylaminomethyl, methylaminoethyl, ethylaminomethyl, ethylaminoethyl and isopropylaminoethyl, $(R^5)HN$—$(CH_2)_q$, Y—$(CH_2)_m$—$NR^5$—$(CH_2)_q$, $C_{4-20}$-hetarylalkyl such as 2-pyridylmethyl, 2-furanylmethyl, 3-pyrrolylmethyl and 2-imidazolylmethyl, $C_{4-20}$-alkylhetaryl such as 2-methyl-3-pyridinyl, 4,5-dimethyl-2-imidazolyl, 3-methyl-2-furanyl and 5-methyl-2-pyrazinyl, hetaryl such as 2-pyridinyl, 3-pyridinyl, 4-pyridinyl, pyrazinyl, 3-pyrrolyl, 2-imidazolyl, 2-furanyl and 3-furanyl, $R^1$, $R^2$, $R^3$, $R^4$ $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl, cyclohexyl and cyclooctyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6- trimethylphenyl, 2-ethylphenyl, 3-ethylphenyl, 4-ethylphenyl, 2-n-propylphenyl, 3-n-propylphenyl and 4-n-propylphenyl, $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together a —$(CH_2)_j$—X—$(CH_2)_m$— group, such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—NR$^5$—$(CH_2)_2$—, —$(CH_2)_2$—O—$(CH_2)_2$—, —$(CH_2)_2$—NR$^5$—$(CH_2)_2$—, —$CH_2$—O—$(CH_2)_3$—, —$CH_2$—NR$^5$—$(CH_2)_3$—, $R^1$, $R^2$ $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_{1-4}$-alkyl such as methyl, ethyl, n-propyl, isopropyl, n-butyl, isobutyl, sec-butyl and tert-butyl, $R^1$ and $R^2$ together a —$(CH_2)_j$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—NR$^5$—$(CH_2)_2$—, —$(CH_2)_2$—O—$(CH_2)_2$—, —$(CH_2)_2$—NR$^5$—$(CH_2)_2$—, —$CH_2$—O—$(CH_2)_3$—, —$CH_2$—NR$^5$—$(CH_2)_3$—, $R^5$, $R^{10}$ $C_{1-4}$-alkyl, such as methyl, ethyl, n-propyl, isopropyl, n-butyl, isobutyl, sec-butyl and tert-butyl, preferably methyl and ethyl, particularly preferably methyl, $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, $R^6$, $R^7$, $R^8$, $R^9$ methyl and ethyl, preferably methyl,

X $CH_2$, $CHR^5$, oxygen or $NR^5$,

Y $N(R^{10})_2$, hydroxyl, $C_{2-20}$-alkylaminoalkyl, preferably $C_{2-16}$-alkylaminoalkyl, such as methylaminomethyl, methylaminoethyl, ethylaminomethyl, ethylaminoethyl and isopropylaminoethyl, $C_{3-20}$-dialkylaminoalkyl, preferably $C_{3-16}$-dialkylaminoalkyl such as dimethylaminomethyl, dimethylaminoethyl, diethylaminoethyl, di-n-propylaminoethyl and diisopropylaminoethyl, j, l an integer from 1 to 4 such as 1, 2, 3 and 4, preferably 2 and 3, particularly preferably 2, k, m, q an integer from 1 to 4 such as 1, 2, 3 and 4, preferably 2, 3 and 4, particularly preferably 2 and 3, n an integer from 1 to 10, preferably an integer from 1 to 8 such as 1, 2, 3, 4, 5, 6, 7 or 8, particularly preferably an integer from 1 to 6 such as 1, 2, 3, 4, 5 or 6.

Ketones which are suitable for use in the process according to the invention are virtually all aliphatic and aromatic ketones. The aliphatic ketones may be straight-chain, branched or cyclic, and the ketones may contain heteroatoms. To date no restrictions are known on the number of carbons in the ketones which can be aminated. The ketones may moreover have substituents which are inert under the conditions of the hydrogenating amination, for example alkoxy, alkenyloxy, alkylamino or dialkylamino groups. If it is intended to aminate polyfunctional ketones, it is possible by controlling the reaction conditions to obtain amino alcohols, cyclic amines or polyaminated products.

Examples of ketones which preferably undergo the aminating hydrogenation are the following:

acetone, ethyl methyl ketone, methyl vinyl ketone, isobutyl methyl ketone, 3-methyl-2-butanone, diethyl ketone, tetralone, acetophenone, p-methylacetophenone, p-methoxyacetophenone, n-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Aldehydes suitable for use in the process according to the invention are virtually all aliphatic and aromatic aldehydes. The aliphatic aldehydes may be straight-chain, branched or cyclic, and the aldehydes may contain heteroatoms. To date no restrictions are known on the number of carbons in the aldehydes which can be aminated. The aldehydes may moreover have substituents which are inert under the conditions of the hydrogenating amination, for example alkoxy, alkenyloxy, alkylamino or dialkylamino groups. If it is intended to aminate polyfunctional aldehydes or keto aldehydes, it is possible by controlling the reaction conditions to obtain amino alcohols, cyclic amines or polyaminated products.

Examples of aldehydes which preferably undergo the aminating hydrogenation are the following: formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-aminopropionaldehyde, hyderoxypivalaldehyde, dimethylolpropionaldehyde, dimethylolbutyraldehyde, furfural, glyoxal and hydroformylated oligomers and polymers such as hydroformylated polyisobutene (polyisobutenealdehyde, PIBA) or oligomer obtained by metathesis with 1-pentene and cyclopentene and hydroformylated.

The aminating agents which can be employed in the hydrogenating amination of aldehydes and ketones are both ammonia and primary or secondary, aliphatic or cycloaliphatic amines.

For use of ammonia as aminating agent, the carbonyl groups are initially converted into free amino groups (—$NH_2$). The primary amines formed in this way can react with hydroxyl or further carbonyl groups to give the corresponding secondary amines, and these in turn can react with hydroxyl or further carbonyl groups to give the corresponding symmetrical tertiary amines. It is possible in this way to prepare as required preferentially primary, secondary or tertiary amines, depending on the composition of the reaction mixture and on the reaction conditions used—pressure, temperature, reaction time.

It is possible in this way to prepare from polyfunctional aldehydes or ketones by intramolecular hydrogenating amination cyclic amines such as pyrrolidines, piperidines, hexamethyleneimines, piperazines and morpholines.

Primary or secondary amines can be used as aminating agents just like ammonia.

These aminating agents are preferably used to prepare asymmetrically substituted di- or trialkylamines such as ethyldiisopropylamine and ethyldicyclohexylamine. Examples of mono- and dialkylamines which are preferably used as aminating agents are the following: methylamine, dimethylamine, ethylamine, diethylamine, propylamine, diisopropylamine, butylamine, pentylamine, hexylamine and cyclohexylamine.

The aminating agent can be employed in stoichiometric amount relative to the carbonyl group which is to undergo aminating hydrogenation. However, an excess of aminating agent is preferably used, generally a more than 5 molar excess per mole of carbonyl group which is to undergo aminating hydrogenation. Ammonia in particular is generally employed in a 5 to 250-fold, preferably 10 to 100-fold, in particular 25 to 80-fold, molar excess per mole of carbonyl groups to be reacted. Larger excesses of ammonia and of primary or secondary amines are possible.

The process according to the invention can be carried out batchwise or, preferably, continuously as follows, with the catalyst preferably being arranged as fixed bed in the reactor.

Amination of the aldehyde groups or keto groups in the precursor can be carried out in the liquid phase or in the gas phase.

The reaction is normally carried out at temperatures from 80 to 250° C., preferably 80 to 230° C., particularly preferably 80 to 200° C., very particularly preferably 80 to 155° C.

The reaction is generally carried out under a pressure of 1 to 400 bar (0.1 to 40 MPa). Pressures of 10 to 250 bar, in particular of 20 to 200 bar, are preferably used.

It is possible to use higher temperatures and a higher total pressure. The total pressure in the reaction vessel, which derives from the total of the partial pressures of the aminating agent, of the carbonyl component, of the reaction products and of the solvent which is also used where appropriate, at the stated temperatures, is expediently adjusted by injecting hydrogen to the pressure required for the reaction.

The amount of hydrogen generally fed into the reaction is 5 to 400 l(STP), preferably 50 to 200 l(STP), per mole of carbonyl component, the liter data having been in each case converted to standard conditions (S.T.P.).

The reaction generally takes place without additional solvent. When reacting high molecular weight starting compounds or products which have high viscosity or are solid at room temperature it may be advantageous also to use a solvent which is inert under the reactions conditions, such as methanol, ethanol, propanol, tetrahydrofuran, dioxane, N-methylpyrrolidone, mihagol or ethylene glycol dimethyl ether.

It may be advantageous for the selectivity of the present process to mix the catalyst shaped articles in the reactor with inert packings in order as it were to dilute them. The proportion of the packings in such catalyst preparations can be 20 to 80, especially 30 to 60 and, in particular, 40 to 50 parts by volume.

The procedure in practice is generally to feed the aldehyde or the ketone and the aminating agents simultaneously into the catalyst, which is normally present in a fixed bed reactor, preferably heated from outside, and which is at the required reaction temperature and the required pressure. The space velocity in this case is generally from 0.02 to 3, preferably 0.05 to 2, particularly preferably 0.1 to 1.6, 1 of aldehyde or ketone per liter of catalyst and hour. It is expedient in this connection to heat the reactants before feeding into the reaction vessel, preferably to the reaction temperature.

The reactants can be passed either upwards or else downwards through the reactor. It is self-evident that the process can be carried out either batchwise or continuously. In both cases, the excess aminating agent can be recycled together with the hydrogen. If the conversion in the reaction is not complete, the unreacted starting material can likewise be fed back into the reaction zone.

After expediently decompressing the discharge from the reactor, the excess aminating agent and the hydrogen are removed, and the resulting aminated products are purified by distillation, liquid extraction or crystallization.

The excess aminating agent and hydrogen are advantageously fed back into the reaction zones. The same applies to any unreacted or incompletely reacted carbonyl component or alcohol produced by hydrogenation.

The water formed during the reaction generally has no adverse effect on the degree of conversion, the reaction rate, the selectivity and the catalyst life and is therefore expediently removed from the reaction product only when it is worked up by distillation.

The amines obtainable by the process according to the invention are suitable inter alia as intermediates in the preparation of fuel additives (U.S. Pat. No. 3,275,554; DE-A-21 25 039 and DE-A-36 11 230), surfactants, drugs and crop protection agents, and of vulcanization accelerators.

EXAMPLES

Preparation of Catalyst A

An aqueous solution of nickel nitrate, copper nitrate and zirconium acetate containing 4.48% NiO, 1.52% CuO and 2.82% $ZrO_2$ was precipitated with a 20% strength aqueous sodium carbonate solution simultaneously at a constant flow rate in a stirred vessel at a temperature of 70° C. in such a way that the pH of 7.0 measured with a glass electrode was maintained.

The resulting suspension was filtered, and the filter cake was washed with deionized water until the electrical conductivity of the filtrate was about 20 mS. Then 1.5% $MoO_3$ were stirred in as aqueous solution of ammonium heptamolybdate. The filter cake was then dried at a temperature of 150° C. in a drying oven or a spray dryer. The hydroxide/carbonate mixture obtained in this way was then heat-treated at a temperature of 500° C. for a period of 4 hours.

The catalyst obtained in this way had the composition: 51% by weight NiO, 17% by weight CuO, and 30.5% by weight $ZrO_2$ and 1.5% by weight $MoO_3$. The catalyst powder was mixed with 3% by weight graphite and shaped to 6×3 mm tablets.

Determination of the mechanical stability of catalyst A under reaction conditions (boiling test): An autoclave was charged with 30 g of catalyst A (in the basket), 67 ml of morpholine, 67 ml of diethylene glycol and 16 ml of water. The autoclave was closed and flushed with argon. The contents of the autoclave were stirred (700 rpm). Then 50 bar of $H_2$ were injected and the contents of the reactor were heated over the course of 120 min to the required temperature, e.g. 150° C. or 200° C. The pressure was raised with $H_2$ to 200 bar and stirred at the particular temperature for 16 h. Cooling was followed by very slow decompression (over the course of 15 min) so that the reactants present in the catalyst pores do not suddenly evaporate and disintegrate the catalyst tablet. The hardness of the tablets was then checked. As is evident from the following table of results, the catalyst A surprisingly has a considerably higher side crushing strength after the end of tests at temperatures distinctly lower than 200° C., e.g. at temperatures from 80 to 155° C., than after the end of a test at 200° C. This result is consistent with the results on the hydrogenating amination of anisaldehyde (see Example 1).

| Side crushing strength of catalyst A (in Newton [N]) | | |
|---|---|---|
| in reduced form before the boiling test: | after the boiling test at 200 bar and 200° C.: | after the boiling test at 200 bar and 150° C.: |
| 131 | 6 | 30 |

Example 1

General Method for the Continuous Amination of Carbonyl Compounds

A continuously operated pressure reactor was packed with 500 cm$^3$ of catalyst A and charged hourly with carbonyl compound and liquid ammonia. The catalysts were introduced in a reduced and passivated state. The particular reaction conditions were adjusted without after-reduction. The discharges from the reaction were decompressed and then excess ammonia was distilled off. The collected discharges from the reaction were each analyzed by gas chromatography (the settings can be found in the following table):

Continuous Amination of Monomeric Compounds

| Carbonyl compound | Amine | Temp. [° C.] | Pressure [bar] | Space velocity [kg/l*h] | Amine/ carbonyl compound mol/mol | Yield* [%] | Remarks |
|---|---|---|---|---|---|---|---|
| | | | | | | isopropylamine | |
| Acetone | NH$_3$ | 130 | 10 | 0.190 | 5.2 | 95.2 | 3.1% isopropanol, 1.2% diisopropanol |
| Acetone | NH$_3$ | 210 | 25 | 0.380 | 5.2 | 82.3 | 3.3% isopropanol, 13.5% diisopropanol |
| Acetone | NH$_3$ | 210 | 20 | 0.644 | 6.6 | 87.7 | 3.1% isopropanol, 8.4% diisopropanol |
| | | | | | | 4-methoxybenzylamine | |
| Anisaldehyde | NH$_3$ | 120 1) | 200 | 0.6 | 6.5 | 99.2 | 0.5% byproducts |
| | | 130 2) | 200 | 0.6 | 6.5 | 98.6 | 0.7% byproducts |
| | | 200 3) | 200 | 0.6 | 6.5 | 91.3 | 7.5% byproducts |
| | | | | | | cyclopentylamine | |
| Cyclopentanone | NH$_3$ | 150 | 200 | 0.76 | 13.5 | 92 | 6% cyclopentanol |
| Cyclopentanone | NH$_3$ | 160 | 200 | 0.76 | 13.5 | 94 | 4% cyclopentanol |
| Cyclopentanone | NH$_3$ | 170 | 200 | 0.76 | 13.5 | 97 | 1% cyclopentanol |
| | | | | | | propylamines | |
| Propionaldehyde | NH$_3$ | 110 | 140 | 0.48 | 1.2 | 93 | 49% MPA, 40% DPA, 4% TPA, 2% n-propanol |
| Propionaldehyde | NH$_3$ | 150 | 140 | 0.48 | 1.2 | 97 | 53% MPA, 39% DPA, 5% TPA, 1% n-propanol |
| | | | | | | 3-pentylamine | |
| Diethyl ketone | NH$_3$ | 130 | 70 | 0.33 | 6.5 | 96 | 3% 3-pentanol |
| | | | | | | 2-butylamine | |
| Methyl ethyl ketone | NH$_3$ | 160 | 200 | 0.48 | 10 | 95 | 2% sec. butanol |
| Methyl ethyl ketone | NH$_3$ | 180 | 200 | 0.48 | 10 | 96 | 2% sec. butanol |

*There was complete conversion in all the reactions

Notes for the reactions of anisaldehyde with ammonia:
1) The side crushing strength of the catalyst removed after the end of the test was 48 N.
2) The side crushing strength of the catalyst removed after the end of the test was 37 N.
3) The side crushing strength of the catalyst removed after the end of the test was 5 N.

Example 2
Continuous Amination of Polyisobutenealdehyde

A continuously operated high pressure reactor was packed with 500 cm³ of catalyst A and charged hourly with 500/750/1000 cm³ of polyisobutene-oxo aldehyde (45% by weight solution in mihagol, CO value: 13 mg KOH/g, OH value: 17 mg KOH/g) and 280/425/565 cm³ of liquid ammonia. The catalyst temperature was adjusted to 190° C., and the pressure in the reactor was adjusted to 200 bar by simultaneous injection of hydrogen. The discharge from the reactor was decompressed and then excess ammonia was distilled off. Analysis gave the following results:

Amination of hydroformylated polyisobutene (45% by weight in mihagol) at 190° C./200 bar with ammonia:

| Space velocity [kg/1*h] | Amine/carbonyl [mol/mol] | OH value [mg KOH/g] | CO value [mg KOH/g] | Amine value [mg KOH/g] | 2° + 3° amine value [mg KOH/g] | Acetyl value [mg KOH/g] |
|---|---|---|---|---|---|---|
| Pib-Oxo |  | 17 | 13 |  |  |  |
| 0.8 | 80 | <1 | <1 | 22 | 2 | 24 |
| 1.2 | 80 | <1 | <1 | 22 | 1 | 22 |
| 1.6 | 80 | <1 | <1 | 21 | 1 | 23 |

Example 3
Batchwise Amination of Hydroformylated Cyclopentene Oligomer with Ammonia 1. The reduced and passivated catalyst A (15 ml) was, after introduction into a catalyst basket and checking the autoclave (300 ml stirred autoclave) for leaks, heated under a pressure of 20 bar of hydrogen to 200° C., setting up a pressure of about 30 to 39 bar. This was then increased to 100 bar with hydrogen, and the catalyst was activated. After 16 h at 200° C. the autoclave was cooled and decompressed. After activation of the catalyst, the pressure vessel was evacuated and 50 ml of the precursor to be reacted (hydroformylated oligomer obtained by metathesis of 1-pentene and cyclopentene, see following table for characteristic values) was sucked as a 30% solution in tetrahydrofuran into the autoclave with exclusion of air and venting with nitrogen. Then 73 ml of ammonia and 30 bar of hydrogen were injected and, after heating to the final temperature (185° C.), further hydrogen was injected to the final pressure (200 bar), and the reaction was carried out for 20 h. The autoclave was then cooled and decompressed, and its contents were dissolved out with THF. After removal of the solid constituents by filtration and removal of the THF in a rotary evaporator, 18.3 g of a colorless liquid product were obtained.

2. 15 ml of catalyst A were reduced/passivated and introduced for immediate startup, and 60 ml of precursor (hydroformylated oligomer obtained by metathesis of 1-pentene and cyclopentene, see following table for characteristic values) were reacted as 50% strength solution in tetrahydrofuran with 50 ml of ammonia analogously on this catalyst at 200° C. and 220 bar for 20 h. The autoclave was then cooled and decompressed and its contents were removed with THF. After removal of the solid constituents by filtration and removal of the THF in a rotary evaporator, 20.3 g of a colorless liquid product were obtained; the characteristic values are shown in the following table.

3. 150 ml of catalyst A after reduction/passivation were introduced into a catalyst basket in a 2.5 l stirred autoclave for immediate startup, and 600 ml of precursor (hydroformylated oligomer obtained by metathesis of 1-pentene and cyclopentene, see Table 3 for characteristic values) were reacted as 50% strength solution in tetrahydrofuran with 500 ml of ammonia analogously on this catalyst at 200° C. and 220 bar for 48 h. The autoclave was then cooled and decompressed, and its contents were dissolved out with toluene. The solid constituents were removed by filtration, and the solvent was removed in a rotary evaporator, resulting in 314 g of a colorless liquid; the characteristic values are shown in the following table.

Batchwise Amination of Hydroformylated Cyclopentene Oligomer

| Precursor: NH₃ ratio | Temp. [° C.] | Pressure [bar] | Time [h] | OH value [mg KOH/g] | CO value [mg KOH/g] | Amine value [mg KOH/g] | Tert. amine value [mg KOH/g] |
|---|---|---|---|---|---|---|---|
| 1:0 |  |  |  | 27 | 307 | 0 | 0 |
| 1:25 | 185 | 200 | 20 | 33 | 3 | 252.7 | 7 |
| 1:10 | 200 | 220 | 20 | <1 | <1 | 231.5 | 9.9 |
| 1:10 | 200 | 220 | 48 | 15 |  | 264 | 12.4 |

Example 4
General Method for Batchwise Aminating Hydrogenation 30 g of catalyst A were introduced into a 1.2 l autoclave and ammonia was injected under a nitrogen atmosphere. After heating to 150° C. (pressure about 170 bar), the carbonyl compound was pumped in over the course of 1 h (temporary rise in pressure over 220 bar; in the case of high-boiling ketones, the precursor was introduced together with the catalyst) and then stirred for 1 h. Hydrogenation was then carried out in the presence of hydrogen under a total pressure of up to 250 bar until the pressure was constant for 3 h (time: 11 to 15 h). The catalyst was employed in each case in reduced and passivated powder form. The composition of the discharges from the reaction was determined by gas chromatography (column: 50 m OV 1701).

Batchwise Amination of Monomeric Compounds

| Carbonyl compound | Amine | Precursor: NH$_3$ molar ratio | Temp. [° C.] | Pressure [bar] | Time [h] | Conversion [%] | Selectivity [%] | Remarks [%] |
|---|---|---|---|---|---|---|---|---|
| p-methoxyacetophenone | NH$_3$ | 1:10 | 150 | 150 | 10 | 98.6 | 1-(p-methoxy-phenyl)ethylamine 94.7 | in methanol |
| m-methoxyacetophenone | NH$_3$ | 1:10 | 150 | 150 | 5 | 98.1 | 1-(m-methoxy-phenyl)ethylamine 98 | in methanol |
| 2-acetylnaphthalene | NH$_3$ | 1:10 | 150 | 80 | 3 | >99.9 | β-nephthylethylamine 88.8 | in methanol. 9.4 alcohol |
| 1-acetylnaphthalene | NH$_3$ | 1:10 | 150 | 85 | 5 | >99.9 | α-naphthylethylamine 93.7 | in methanol. 4.7 alcohol |
| p-methylacetophenone | NH$_3$ | 1:10 | 150 | 150 | 12 | >99.9 | 1-(p-tolyl)ethylamine 97.5 | in methanol |
| tetralone | NH$_3$ | 1:10 | 150 | 150 | 7 | >99.9 | 1,2,3,4-tetrahydro-1-naphtylamine 97.1 | in methanol |
| methyl ethyl ketone | CH$_3$NH$_2$ | 1:1.33 | 80 | 56 | 12 | 99.75 | 2-butylamine 84.4 | 16.5 alcohol |
| acetone | isopropylamine | 3 | 130 | 200 | 4 | 100 | diisopropylamine 40 | 60 isopropanol |
| acetone | isopropylamine | 3 | 200 | 200 | 4 | 100 | 70 | 30 isopropanol |
| acetone | isopropylamine | 3 | 200 | 200 | 12 | 100 | 98 | 2 isopropanol |

Comparative Examples

Method for Continuous Amination of Acetone

A continuously operated reactor (pressure 10 to 25 bar) was packed with 100 cm³ of catalyst A and charged with acetone and ammonia. The catalysts were introduced in reduced and passivated form. Without after-reduction, the particular reaction conditions were set and maintained until conversion was complete. The discharges from the reaction were decompressed and excess ammonia was then distilled out. The collected discharges from the reaction were in each case analyzed by gas chromatography. The particular reaction conditions and results are compiled in the following table.

Composition of cat. B: 47% by weight CuO, 10% by weight NiO, 43% by weight Al$_2$O$_3$ Composition of cat. C: 53% by weight CuO, 47% by weight TiO$_2$ The comparison shows that catalyst A has the highest selectivity for preparing monoisopropylamine. In addition, the content of unwanted alcohol (isopropanol) is least with catalyst A. Catalyst C in particular shows a strong tendency to form secondary amines.

TABLE

| Temp. [° C.] | Pressure [bar] | Catalyst | Acetone [g/h] | Space velocity [kg/l*h] | NH$_3$ [g/h] | H$_2$ [l(STP)/h] | NH$_3$/ acetone mol/mol | GC analysis (% area) | | | |
|---|---|---|---|---|---|---|---|---|---|---|---|
| | | | | | | | | Isopropyl-amine | Iso-propanol | Diisopropyl-amine | Total |
| 130 | 10 | B | 9.5 | 0.190 | 14 | 10 | 5.0 | 93.7 | 3.5 | 2.3 | 99.5 |
| 130 | 10 | C | 9.5 | 0.190 | 14.5 | 10 | 5.2 | 20 | 15.6 | 64.3 | 99.9 |
| 130 | 10 | A | 9.5 | 0.190 | 14.6 | 10 | 5.2 | 95.2 | 3.1 | 1.2 | 99.5 |
| 210 | 25 | B | 19 | 0.380 | 29.2 | 10 | 5.2 | 76.4 | 3.7 | 18.8 | 98.9 |
| 210 | 25 | C | 19 | 0.380 | 29 | 20 | 5.2 | 62.6 | 5.4 | 30.5 | 98.5 |
| 210 | 25 | A | 19 | 0.380 | 29 | 20 | 5.2 | 82.3 | 3.3 | 13.5 | 99.1 |
| 210 | 20 | B | 30 | 0.600 | 62 | 30 | 7.1 | 85.5 | 2.6 | 11.2 | 99.3 |
| 210 | 20 | C | 30 | 0.600 | 61.6 | 30 | 7.0 | 53.1 | 8.6 | 36.7 | 98.4 |
| 210 | 20 | A | 32.2 | 0.644 | 62 | 30 | 6.6 | 87.7 | 3.8 | 8.4 | 99.2 | l(STP) = liters converted to standard conditions
Space velocity in kg of precursor per liter of catalyst and hour.

We claim:

1. A process for preparing amines by reacting aldehydes or ketones at elevated temperature under elevated pressure with nitrogen compounds selected from the group of ammonia, primary and secondary amines, and with hydrogen in the presence of a catalyst containing copper, wherein the catalytically active mass of the catalyst contains, before the reduction with hydrogen, 20 to 85% by weight of oxygen-containing compounds of zirconium, calculated as $ZrO_2$, 1 to 30% by weight of oxygen-containing compounds of copper, calculated as CuO, 14 to 70% by weight of oxygen-containing compounds of nickel, calculated as NiO, 0 to 5% by weight of oxygen-containing compounds of molybdenum, calculated as $MoO_3$, and 0 to 10% by weight of oxygen-containing compounds of aluminum, calculated as $Al_2O_3$.

2. A process as claimed in claim 1, wherein the catalytically active mass of the catalyst contains, before the reduction with hydrogen, 0.1 to 5% by weight of oxygen-containing compounds of molybdenum, calculated as $MoO_3$.

3. A process as claimed in claim 1, wherein the catalytically active mass of the catalyst contains, before the reduction with hydrogen, 22 to 65% by weight of oxygen-containing compounds of zirconium, calculated as $ZrO_2$, 5 to 25% by weight of oxygen-containing compounds of copper, calculated as CuO, 29.7 to 70% by weight of oxygen-containing compounds of nickel, calculated as NiO, 0.3 to 3.5% by weight of oxygen-containing compounds of molybdenum, calculated as $MoO_3$, and 0 to 10% by weight of oxygen-containing compounds of aluminum, calculated as $Al_2O_3$.

4. A process as claimed in claim 1, wherein the catalytically active mass of the catalyst contains, before the reduction with hydrogen, 25 to 49.7% by weight of oxygen-containing compounds of zirconium, calculated as $ZrO_2$, 10 to 25% by weight of oxygen-containing compounds of copper, calculated as CuO, 40 to 60% by weight of oxygen-containing compounds of nickel, calculated as NiO, 0.3 to 3.5% by weight of oxygen-containing compounds of molybdenum, calculated as $MoO_3$, and 0 to 5% by weight of oxygen-containing compounds of aluminum, calculated as $Al_2O_3$.

5. A process as claimed in claim 1, wherein the reaction is carried out under pressures of from 0.1 to 40 MPa.

6. A process as claimed in claim 1, wherein the reaction is carried out at temperatures of from 80 to 250° C.

7. A process as claimed in claim 1, wherein the reaction is carried out at temperatures of from 80 to 155° C.

8. A process as claimed in claim 1, wherein the catalyst is employed in the form of shaped articles.

9. A process as claimed in claim 1 for preparing amines of the formula I

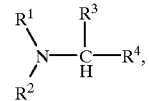
(I)

in which

R$^1$, R$^2$ are hydrogen, $C_{1-20}$-alkyl, $C_{3-12}$-cycloalkyl, aryl, $C_{7-20}$-aralkyl and $C_{7-20}$-alkylaryl or together are $(CH_2)_j$—X—$(CH_2)_k$, R$^3$, R$^4$ are hydrogen, alkyl, cycloalkyl, hydroxyalkyl, aminoalkyl, alkanolaminoalkyl, alkoxyalkyl, dialkylaminoalkyl, alkylaminoalkyl, R$^5$—$(OCR^6R^7CR^8R^9)_n$—$(OCR^6R^7)$, aryl, hetaryl, aralkyl, hetarylalkyl, alkylaryl, alkylhetaryl and Y—$(CH_2)_m$—NR$^5$—$(CH_2)_q$ or together $(CH_2)_j$—X—$(CH_2)_m$ or R$^2$ and R$^4$ are together $(CH_2)_j$—X—$(CH_2)_m$, R$^5$, R$^{10}$ are hydrogen, $C_{1-4}$-alkyl, $C_{7-40}$-alkylphenyl, R$^6$, R$^7$, R$^8$, R$^9$ are hydrogen, methyl or ethyl, X is $CH_2$, CHR$^5$, oxygen or NR$^5$, Y is $N(R^{10})_2$, hydroxyl, $C_{2-20}$-alkylaminoalkyl or $C_{3-20}$-dialkylaminoalkyl, n is an integer from 1 to 30 and j, k, l, m, q are an integer from 1 to 4 by reacting aldehydes or ketones of the formula II or III

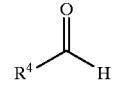
(II)

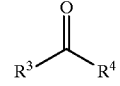
(III)

with nitrogen compounds of the formula IV

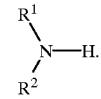
(IV)

10. The process of claim 9, wherein

R$^1$ and R$^2$ are hydrogen, $C_{1-20}$-alkyl, $C_{3-12}$-cycloalkyl, aryl, $C_{7-20}$-aralkyl and $C_{7-20}$-alkyaryl or together are $(CH_2)_j$—X—$(CH_2)_k$, R$^3$ and R$^4$ are hydrogen, $C_1$–$C_{200}$-alkyl, $C_3$–$C_{12}$-cycloalkyl, $C_1$–$C_{20}$-hydroxyalkyl, $C_1$–$C_{20}$-aminoalkyl, $C_1$–$C_{20}$-alkanolaminoalky, $C_2$–$C_{30}$-alkoxyalkyl, $C_3$—$C_{30}$-dialkylaminoalkyl, $C_2$–$C_{30}$-alkylaminoalkyl, R$^5$—$(OCR^6R^7CR^8R^9)_n$—$(OCR^6R^7)$, aryl, hetaryl, $C_7$–$C_{20}$-aralkyl, $C_4$–$C_{20}$-hetarylalkyl, $C_7$–$C_{20}$-alkylaryl, $C_4$–$C_{20}$-alkylhetaryl and Y—$(CH_2)_m$—NR$^5$—$(CH_2)_q$ or together $(CH_2)_j$—X—$(CH_2)_m$ or R$^2$ and R$^4$ are together $(CH_2)_j$—X—$(CH_2)_m$, R$^5$, R$^{10}$ are hydrogen, $C_{1-4}$-alkyl, $C_{7-40}$-alkylphenyl, R$^6$, R$^7$, R$^8$, R$^9$ are hydrogen, methyl or ethyl, X is $CH_2$, CHR$^5$, oxygen or NR$^5$, Y is $N(R^{10})_2$, hydroxyl, $C_{2-20}$-alkylaminoalkyl or $C_{3-20}$-dialkylaminoalkyl, n is an integer from 1 to 30, and j, k, l, m, q are an integer from 1 to 4, and wherein aryl represents an aromatic radical selected from the group of phenyl, naphthyl and anthryl, and hetaryl represents a heteroaromatic radical selected from the group of pyridyl, pyrazinyl, 3-pyrrolyl, 2-imidazolyl and furanyl.

* * * * *

UNITED STATES PATENT AND TRADEMARK OFFICE
CERTIFICATE OF CORRECTION

PATENT NO. : 6,417,353 B1 Page 1 of 1
DATED : July 9, 2002
INVENTOR(S) : Funke et al.

It is certified that error appears in the above-identified patent and that said Letters Patent is hereby corrected as shown below:

Title page,
Item [30], "May 3, 1999" should be -- Mar. 12, 1999 --.

Column 18,
Formula (I) should be as follows:

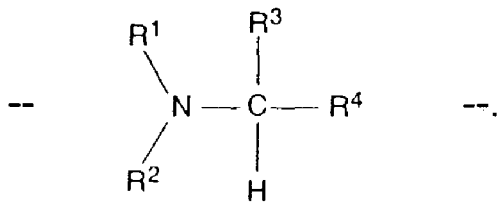

-- ... --.

Line 27, "1;" should be -- 1, --.

Signed and Sealed this

Fourteenth Day of January, 2003

JAMES E. ROGAN
*Director of the United States Patent and Trademark Office*